(12) United States Patent
Schmidt

(10) Patent No.: US 6,884,802 B2
(45) Date of Patent: Apr. 26, 2005

(54) 6-HETEROARYLPHENANTHRIDINES

(75) Inventor: Beate Schmidt, Allensbacher Str. 5 (DE)

(73) Assignee: ALTANA Pharma AG, Constance (DE)

(*) Notice: Subject to any disclaimer, the term of this patent is extended or adjusted under 35 U.S.C. 154(b) by 0 days.

(21) Appl. No.: 10/297,765

(22) PCT Filed: Jul. 7, 2001

(86) PCT No.: PCT/EP01/07818
§ 371 (c)(1),
(2), (4) Date: Dec. 9, 2002

(87) PCT Pub. No.: WO02/06270
PCT Pub. Date: Jan. 24, 2002

(65) Prior Publication Data
US 2004/0038979 A1 Feb. 26, 2004

(30) Foreign Application Priority Data
Jul. 14, 2000 (EP) .............................. 00115352

(51) Int. Cl.$^7$ ................... A61K 31/473; A61K 31/498; C07D 401/04; C07D 405/04; C07D 413/04
(52) U.S. Cl. ................... 514/252.04; 514/256; 514/297; 514/298; 514/255.05; 544/333; 544/405; 544/238; 544/284; 544/353; 546/109; 546/65; 546/74; 546/102
(58) Field of Search ........................... 546/109, 65, 74, 546/102; 544/333, 405, 238, 284, 353; 514/256, 297, 298, 252.04, 255.05

(56) References Cited
FOREIGN PATENT DOCUMENTS

| WO | WO 97/28131 | 8/1997 |
|---|---|---|
| WO | WO 97/35854 | 10/1997 |
| WO | WO 99/05111 | 2/1999 |
| WO | WO 99/05112 | 2/1999 |
| WO | WO 99/05113 | 2/1999 |
| WO | WO 00/42017 | 7/2000 |
| WO | WO 00/42018 | 7/2000 |
| WO | WO 00/42019 | 7/2000 |
| WO | WO 00/42034 | 7/2000 |
| WO | WO 01/51470 | 7/2001 |

OTHER PUBLICATIONS

Burunouf et al. Annual Reports in Medicinal Chemistry, 1998, Academic Press, Chapter 10, pp. 91–109.*
Kametani, T. et al., "Cyclised Products in the Synthesis of 6–Substituted Phenanthridines by Phenolic Cyclisation", *J. Chem. Soc.* ( C ) , pp 1805–1808, (1971).
Govindachari, T.R. et al., "Application of the Bruckner Method to the Synthesis of Phenanthridine Derivatives", *J. Chem. Soc.*, pp. 4280–4283, (1956).
Sugasawa, S. et al., "Synthese Partiell Hydrierter Phenan-thridin–Derivate (I)", *Chem Ber.*, pp. 675–678, (1939).

* cited by examiner

*Primary Examiner*—Evelyn Mei Huang
(74) *Attorney, Agent, or Firm*—Nath & Associates PLLC; Gary M. Nath; Sheldon M. McGee

(57) ABSTRACT

Compounds of formula 1, in which Het is an unsubstituted or R6- and/or R7-substituted pyrrolyl, furanyl, thiophenyl, pyrazolyl, imidazolyl, oxazolyl, isoxazolyl, thiazolyl, isothiazolyl, thiadiazolyl, pyrimidinyl, pyrazinyl or pyradazinyl radical, or an unsubstituted or R6- and/or R7-substituted fused bi- or tricyclic ring system comprising at least one aromatic ring and up to 4 heteroatoms-selected from the group consisting of O (oxygen), S (sulfur), N (nitrogen)- which is bonded to the phenanthridinyl radical via one of the rings comprising one or more heteroatoms, are active PDE4 inhibitors.

11 Claims, No Drawings

6-HETEROARYLPHENANTHRIDINES

This application is a 371 of PCT/EP01/07818, filed on Jul. 7, 2001, the contents of which are incorporated by reference herein in its entirety, which claims the priority of EP 00115352.7, filed on Jul. 14, 2001.

FIELD OF APPLICATION OF THE INVENTION

The invention relates to novel 6-heteroarylphenanthridines, which are used in the pharmaceutical industry for the production of medicaments.

KNOWN TECHNICAL BACKGROUND

Chem.Ber. 1939, 72, 675–677, J. Chem. Soc., 1956, 4280–4283 and J. Chem. Soc.(C), 1971, 1805 describe the synthesis of 6-phenylphenanthridines. The International Applications WO 97/28131, WO 97/35854, WO 99/05111 and WO 99/05113 describe 6-phenyl- and 6-pyridylphenanthridines as PDE4 inhibitors.

DESCRIPTION OF THE INVENTION

It has now been found that the novel phenanthridines substituted in position 6 by a bi- or tricyclic heteroaryl radical and described in greater detail below have surprising and particularly advantageous properties.

The invention thus relates to compounds of the formula I, (I)

in which
- R1 is hydroxyl, 1–4C-alkoxy, 3–7C-cycloalkoxy, 3–7C-cycloalkylmethoxy or completely or predominantly fluorine-substituted 1–4C-alkoxy,
- R2 is hydroxyl, 1–4C-alkoxy, 3–7C-cycloalkoxy, 3–7C-cycloalkylmethoxy or completely or predominantly fluorine-substituted 1–4C-alkoxy,
or in which
- R1 and R2 together are a 1–2C-alkylenedioxy group,
- R3 is hydrogen or 1–4C-alkyl,
- R31 is hydrogen or 1–4C-alkyl,
or in which
- R3 and R31 together are a 1–4C-alkylene group,
- R4 is hydrogen or 1–4C-alkyl,
- R5 is hydrogen,
- R51 is hydrogen,
or in which
- R5 and R51 together represent an additional bond,
- Het is an unsubstituted or R6- and/or R7-substituted pyrrolyl, furanyl, thiophenyl, pyrazolyl, imidazolyl, oxazolyl, isoxazolyl, thiazolyl, isothiazolyl, thiadiazolyl, pyrimidinyl, pyrazinyl or pyridazinyl radical, or an unsubstituted or R6- and/or R7-substituted fused bi- or tricyclic ring system comprising at least one aromatic ring and up to 4 heteroatoms—selected from the group consisting of O (oxygen), S (sulphur) or N (nitrogen)—which is bonded to the phenanthridinyl radical via one of the rings comprising one or more heteroatoms, where
- R6 is hydroxyl, halogen, nitro, cyano, amino, aminocarbonyl, mono- or di-1–4C-alkylamino, mono- or di-1–4C-alkylaminocarbonyl, 1–4C-alkyl, trifluromethyl, 1–4C-alkoxy, 1–4C-alkoxycarbonyl, 1–4C-alkylcarbonyloxy, 1–4C-alkylcarbonyl, 1–4C-alkoxycarbonylamino, phenyl or completely or predominantly fluorine-substituted 1–4C-alkoxy, and
- R7 is hydroxyl, halogen, nitro, 1–4C-alkyl or 1–4C-alkoxy, and the salts, the N-oxides and the salts of the N-oxides of these compounds.

1–4C-Alkyl represents a straight-chain or branched alkyl radical having 1 to 4 carbon atoms. Examples which may be mentioned are the butyl, isobutyl, sec-butyl, tert-butyl, propyl, isopropyl and preferably the ethyl and methyl radicals.

1–4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isbpropoxy and preferably the ethoxy and methoxy radicals.

3–7C-Cycloalkoxy represents cyclopropyloxy, cyclobutyloxy, cyclopentyloxy, cyclohexyloxy and cycloheptyloxy, of which cyclopropyloxy, cyclobutyloxy and cyclopentyloxy are preferred.

3–7C-Cycloalkylmethoxy represents cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

As completely or predominantly fluorine-substituted 1–4C-alkoxy, for example, the 2,2,3,3,3-pentafluoropropoxy, the perfluoroethoxy, the 1,2,2-trifluoroethoxy, in particular the 1,1,2,2-tetrafluoroethoxy, the 2,2,2-trifluoroethoxy, the trifluoromethoxy and preferably the difluoromethoxy radicals may be mentioned. "Predominantly" in this connection means that more than half of the hydrogen atoms of the 1–4C-alkoxy radical are replaced by fluorine atoms.

1–2C-Alkylenedioxy represents, for example, the methylenedioxy [—O—CH$_2$—O—] and the ethylenedioxy [—O—CH$_2$—CH$_2$—O—] radicals.

If R3 and R31 together have the meaning 1–4C-alkylene, the positions 1 and 4 in compounds of the formula I are linked to one another by a 1–4C-alkylene bridge, 1–4C-alkylene representing straight-chain or branched alkylene radicals having 1 to 4 carbon atoms. Examples which may be mentioned are the radicals methylene [—CH$_2$—], ethylene [—CH$_2$—CH$_2$—], trimethylene [—CH$_2$—CH$_2$—CH$_2$—], 1,2-dimethylethylene [—CH(CH$_3$)—CH(CH$_3$)—] and isopropylidene [—C(CH$_3$)$_2$—].

If R5 and R51 together are an additional bond, then the carbon atoms in positions 2 and 3 in compounds of the formula I are linked to one another via a double bond.

Halogen within the meaning of the invention is bromine, chlorine or fluorine.

In addition to the nitrogen atom, mono- or di-1–4C-alkylamino radicals contain one or two of the abovementioned 1–4C-alkyl radicals. Di-1–4C-alkylamino is preferred and here, in particular, dimethyl-, diethyl- or diisopropylamino.

In addition to the carbonyl group, mono- or di-1–4C-alkylaminocarbonyl radicals contain one of the abovementioned mono- or di-1–4C-alkylamino radical. Examples which may be mentioned are the N-methyl-, the N,N-dimethyl-, the N-ethyl-, the N-propyl-, the N,N-diethyl- and N-isopropylaminocarbonyl radicals.

1–4C-Alkylcarbonyloxy represents a carbonyloxy group to which one of the abovementioned 1–4C-alkyl radicals is bonded. An example which may be mentioned is the acetoxy radical [CH$_3$C(O)—O—].

1–4-Alkylcarbonyl represents a radical which, in addition to the carbonyl group, contains one of the 1–4C-alkyl radicals mentioned above. An example which may be mentioned is the acetyl radical.

1–4C-Alkoxycarbonyl represents a carbonyl group to which one of the abovementioned 1–4C-alkoxy radicals is bonded. Examples which may be mentioned are the methoxycarbonyl [CH$_3$O—C(O)—] and the ethoxycarbonyl [CH$_3$CH$_2$O—C(O)—] radicals.

As a 1–4C-alkylcarbonylamino radical, for example, the propionylamino radical [C$_3$H$_7$C(O)NH—] and the acetylamino radical [CH$_3$C(O)NH—] may be mentioned.

Het represents an unsubstituted or R6- and/or R7- substituted pyrrolyl, furanyl, thiophenyl, pyrazolyl, imidazolyl, oxazolyl, isoxazolyl, thiazolyl, isothiazolyl, thiadiazolyl, pyrimidinyl, pyrazinyl or pyridazinyl radical, or an unsubstituted or R6- and/or R7-substituted fused bi- or tricyclic ring system comprising at least one aromatic ring and up to 4 heteroatoms—selected from the group consisting of O (oxygen), S (sulphur) or N (nitrogen)—which is bonded to the phenanthridinyl radical via one of the rings comprising one or more heteroatoms.

Exemplary unsubstituted heteroaryl radicals Het which may be mentioned are benzofuran-2-yl, benzofuran-3-yl, 2,3-dihydrobenzofuran-2-yl, 2,3-dihydrobenzofuran-3-yl, benzothiophen-2-yl, benzothiophen-3-yl, 2,3-dihydrobenzothiophen-2-yl, 2,3-dihydrobenzothiophen-3-yl, chroman-2-yl, chroman-3-yl, chroman-4-yl, isochroman-1-yl, 1,4-benzodioxan-2-yl, 1,3-benzodioxol-2-yl, quinolin-2-yl, quinolin-4-yl, quinolin-3-yl, isoquinolin-3-yl, isoquinolin-1-yl, isoquinolin-4-yl, 1,2,3,4-tetrahydroacridin-9-yl, acridin-9-yl, indolizin-2-yl, indolizin-3-yl, indolizin-5-yl, indolizin-6-yl, indolizin-7-yl, indolizin-8-yl, phenanthridin-6-yl, cinnolin-3-yl, cinnolin-4-yl, quinazolin-4-yl, quinoxalin-2-yl, phthalazin-1-yl, 1,7-naphthyridin-3-yl, 1,6-naphthyridin-3-yl, 1,6-naphthyridin-4-yl, 1,6-naphthyridin-5-yl, 1,5-naphthyridin-2-yl, 1,5-naphthyridin-3-yl, 1,5-naphthyridin-4-yl, 1,5-naphthyridin-6-yl, 1,5-naphthyridin-7-yl, 1,5-naphthyridin-8-yl, indol-3-yl, indol-2-yl, indazol-3-yl, benzimidazol-2-yl, 2,3-dihydro-1H-indol-2-yl, 2,3-dihydro-1H-indol-3-yl, 2,3-dihydro-1H-isoindol-1-yl, 2,3-dihydro-1H-isoindol-3-yl, 1,2,3,4-tetrahydroquinolin-2-yl, 1,2,3,4-tetrahydroquinolin-3-yl, 1,2,3,4-tetrahydroquinolin-4-yl, 1,2,3,4-tetrahydroisoquinolin-1-yl, 1,2,3,4-tetrahydroisoquinolin-3-yl, 1,2,3,4-tetrahydroisoquinolin-4-yl, β-carbolin-1-yl, β-carbolin-3-yl, β-carbolin-4-yl, furan-2-yl, furan-3-yl, thiophen-2-yl, thiophen-3-yl, 1H-pyrrol-2-yl, 1H-pyrrol-3-yl, pyrazol-3-yl, pyrazol-4-yl, imidazol-2-yl, imidazol-4-yl, imidazol-5-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, [1,2,3]thiadiazol-4-yl, [1,2,3]thiadiazol-5-yl, pyrimidin-4-yl, pyrimidin-5-yl, pyrimidin-2-yl, pyridazin-4-yl, pyridazin-3-yl and pyrazin-2-yl.

Exemplary R6- and/or R7-substituted heteroaryl radicals Het which may be mentioned are 1-methyl-1H-pyrrol-2-yl, 5-methyl-3-phenylisoxazol-4-yl, 5-methylthiophen-2-yl, 5-fluoro-1H-indol-2-yl, 6-methoxy-1H-indol-2-yl, 3-methyl-furan-2-yl, 3,5-dimethyl-isoxazol-4-yl, 4-phenyl-[1,2,3]thiadiazol-5-yl, 4-methyl[1,2,3]thiadiazol-5-yl, 1,5-dimethyl-1H-pyrazol-3-yl, 3-methyl-benzofuran-2-yl, 5-methoxybenzofuran-2-yl, 7-methoxybenzofuran-2-yl, 7-ethoxybenzofuran-2-yl, 5-chlorobenzofuran-2-yl, 5-nitrobenzofuran-2-yl, 4-chloro-6-nitroquinolin-2-yl, 2-chloroquinolin-4-yl, 6-methoxyquinolin-4-yl, 2-hydroxyquinolin-4-yl, 8-nitroquinolin-4-yl, 2-cyclopropylquinolin-4-yl, 2-cyclohexyl-6-methylquinolin-4-yl, 1-chloroisoquinolin-4-yl, 4-hydroxyquinolin-2-yl, 2,8-dihydroxyquinolin-2-yl, 5-nitroquinolin-2-yl, 4-methoxyquinolin-2-yl, 4-hydroxy-7-chloroquinolin-2-yl, 8-hydroxyquinolin-2-yl, 6,7-dimethoxyisoquinolin-3-yl, 3-hydroxypyrido[1,2-a]indol-10-yl, 1-methylindol-2-yl, 1-methyl-1H-benzo[d]imidazol-2-yl, 1-methylindol-3-yl, 1-methyl-1H-indazol-3-yl, 1-acetyl-1H-indazol-3-yl, 5-methylindol-2-yl, 7-nitroindol-2-yl, 7-methylindol-2-yl, 4,6-dimethoxyindol-2-yl, 5,6-dimethoxyindol-2-yl, 5-methoxyindol-2-yl, 5-hydroxyindol-2-yl, 5-methoxypyrimidin-2-yl, 6-hydroxypyrimidin-4-yl, 2-chloro-6-methylpyrimidin-4-yl, 2,6-bis(dimethylamino)pyrimidin-4-yl, 2,6-dimethoxypyrimidin-4-yl, 5-methylpyrazin-2-yl, 2-methylpyrazin-5-yl, 5-hydroxypyrazin-2-yl, 2-methylaminopyrazin-6-yl, 2-methoxypyrazin-6-yl and 5-chloropyrazin-2-yl.

Possible salts for compounds of the formula I—depending on substitution—are all acid addition salts or all salts with bases. Particular mention may be made of the pharmacologically tolerable salts of the inorganic and organic acids and bases customarily used in pharmacy. Those suitable are, on the one hand, water-soluble and water-insoluble acid addition salts with acids such as, for example, hydrochloric acid, hydrobromic acid, phosphoric acid, nitric acid, sulfuric acid, acetic acid, trifluoroacetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, it being possible to employ the acids in salt preparation—depending on whether a mono- or polybasic acid is concerned and depending on which salt is desired—in an equimolar quantitative ratio or one differing therefrom.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, where here too the bases are employed in salt preparation in an equimolar quantitative ratio or one differing therefrom.

Pharmacologically intolerable salts which can initially be obtained, for example, as process products in the preparation of the compounds according to the invention on an industrial scale are converted into pharmacologically tolerable salts by processes known to the person skilled in the art.

It is known to the person skilled in the art that the compounds according to the invention and their salts, when they are isolated, for example, in crystalline form, can contain various amounts of solvents. The invention therefore also comprises all solvates and in particular all hydrates of the compounds of the formula I, and also all solvates and in particular all hydrates of the salts of the compounds of the formula I.

Compounds of the formula I to be emphasized are those in which

R1 is 1–2C-alkoxy, 3–5C-cycloalkoxy, 3–5C-cycloalkylmethoxy or completely or predominantly fluorine-substituted 1–2C-alkoxy, R2 is 1–2C-alkoxy, 3–5C-cycloalkoxy, 3–5C-cycloalkylmethoxy or completely or predominantly fluorine-substituted 1–2C-alkoxy, R3 is hydrogen, R31 is hydrogen, R4 is hydrogen or 1–2C-alkyl, R5 is hydrogen, R51 is hydrogen, or in which R5 and R51 together represent an additional bond, Het is an unsubstituted or R6- and/or R7-substituted radical selected from the group consisting of benzofuran-2-yl, benzofuran-3-yl, 2,3-dihydrobenzofuran-2-yl, 2,3-dihydrobenzofuran-3-yl, benzothiophen-2-yl, benzothiophen-3-yl, 2,3-dihydrobenzothiophen-2-yl, 2,3-dihydrobenzothiophen-3-yl, chroman-2-yl, chroman-3-yl, chroman-4-yl, isochroman-1-yl, 1,4-benzodioxan-2-yl, 1,3-benzodioxol-2-yl, quinolin-2-yl, quinolin-4-yl, quinolin-3-yl, isoquinolin-3-yl, isoquinolin-1-yl, isoquinolin-4-yl, 1,2,3,4-tetrahydroacridin-9-yl, acridin-9-yl, indolizin-2-yl, indolizin-3-yl, indolizin-5-yl, indolizin-6-yl, indolizin-7-yl, indolizin-8-yl, phenanthridin-6-yl, cinnolin-3-yl, cinnolin-4-yl, quinazolin-4-yl, quinoxalin-2-yl, phthalazin-1-yl, 1,7-naphthyridin-3-yl, 1,6-naphthyridin-3-yl, 1,6-naphthyridin-4-yl, 1,6-naphthyridin-5-yl, 1,5-naphthyridin-2-yl, 1,5-naphthyridin-3-yl, 1,5-naphthyridin-4-yl, 1,5-naphthyridin-6-yl, 1,5-naphthyridin-7-yl, 1,5-naphthyridin-8-yl, indol-3-yl, indol-2-yl, indazol-3-yl, benzimidazol-2-yl, 2,3-dihydro-1H-indol-2-yl, 2,3-dihydro-1H-indol-3-yl, 2,3-dihydro-1H-isoindol-1-yl, 2,3-dihydro-1H-isoindol-3-yl, 1,2,3,4-tetrahydroquinolin-2-yl, 1,2,3,4-tetrahydroquinolin-3-yl, 1,2,3,4-tetrahydroquinolin-4-yl, 1,2,3,4-tetrahydroisoquinolin-1-yl, 1,2,3,4-tetrahydroisoquinolin-3-yl, 1,2,3,4-tetrahydroisoquinolin-4-yl, β-carbolin-1-yl, β-carbolin-3-yl, β-carbolin-4-yl, furan-2-yl, furan-3-yl, thiophen-2-yl, thiophen-3-yl, 1H-pyrrol-2-yl, 1H-pyrrol-3-yl, pyrazol-3-yl, pyrazol-4-yl, imidazol-2-yl, imidazol-4-yl, imidazol-5-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, [1,2,3]thiadiazol-4-yl, [1,2,3]thiadiazol-5-yl, pyrimidin-4-yl, pyrimidin-5-yl, pyrimidin-2-yl, pyridazin-4-yl, pyridazin-3-yl and pyrazin-2-yl, where R6 is hydroxyl, halogen, nitro, amino, aminocarbonyl, 1–4C-alkyl, 1–4C-alkoxy, 1–4C-alkylcarbonyloxy, 1–4C-alkoxycarbonyl or completely or predominantly fluorine-substituted 1–2C-alkoxy, and R7 is hydroxyl, halogen, 1–4C-alkyl or 1–4C-alkoxy, and the salts, the N-oxides and the salts of the N-oxides of these compounds.

Compounds of the formula I to be particularly emphasized are those in which

R1 is 1–2C-alkoxy,

R2 is 1–2C-alkoxy,

R3, R31, R4, R5 and R51 are hydrogen,

Het is an unsubstituted or R6- and/or R7-substituted radical selected from the group consisting of benzofuran-2-yl, benzothiophen-2-yl, quinolin-2-yl, quinolin-4-yl, isoquinolin-1-yl, indol-2-yl, furan-2-yl, furan-3-yl, thiophen-2-yl, thiophen-3-yl, 1H-pyrrol-2-yl, pyrazol-3-yl, thiazol-2-yl, thiazo-3-yl, isoxazol-4-yl, isoxazol-5-yl, [1,2,3]thiadiazol-5-yl and pyrazin-2-yl, where R6 is halogen, 1–4C-alkyl, 1–4C-alkoxy or phenyl, and R7 is 1–4C-alkyl, and the salts, the N-oxides and the salts of the N-oxides of these compounds.

Preferred compounds of the formula I are those in which

R1 is methoxy,

R2 is methoxy,

R3, R31, R4, R5 and R51 are hydrogen, and

Het is quinolin-4-yl, quinolin-2-yl, 3-methyl-furan-2-yl, 3-methyl-benzofuran-2-yl, 7-methoxybenzofuran-2-yl, 5-methoxy-benzofuran-2-yl, thiophen-2-yl, 5-methyl-thiophen-2-yl, thiophen-3-yl, 1H-indol-2-yl, 5-fluoro-1H-indol-2-yl, 6-methoxy-1H-indol-2-yl, and the salts, the N-oxides and the salts of the N-oxides of these compounds.

One embodiment (embodiment A) of the compounds of formula I are those compounds in which R1 is hydroxyl, 1–4C-alkoxy, 3–7C-cycloalkoxy, 3–7C-cycloalkylmethoxy or completely or predominantly fluorine-substituted 1–4C-alkoxy, R2 is hydroxyl, 1–4C-alkoxy, 3–7C-cycloalkoxy, 3–7C-cycloalkylmethoxy or completely or predominantly fluorine-substituted 1–4C-alkoxy, or in which R1 and R2 together are a 1–2C-alkylenedioxy group, R3 is hydrogen or 1–4C-alkyl, R31 is hydrogen or 1–4C-alkyl, or in which R3 and R31 together are a 1–4C-alkylene group, R4 is hydrogen or 1–4C-alkyl, R5 is hydrogen, R51 is hydrogen, or in which R5 and R51 together represent an additional bond, Het is an unsubstituted or R6- and/or R7-substituted pyrimidinyl, pyrazinyl or pyridazinyl radical, or an unsubstituted or R6- and/or R7-substituted fused bi- or tricyclic ring system comprising at least one aromatic ring and up to 4 heteroatoms—selected from the group consisting of O (oxygen) or N (nitrogen)—which is bonded to the phenanthridinyl radical via one of the rings comprising one or more heteroatoms, where R6 is hydroxyl, halogen, nitro, cyano, amino, aminocarbonyl, mono- or di-1–4C-alkylamino, mono- or di-1–4C-alkylaminocarbonyl, 1–4C-alkyl, trifluromethyl, 1–4C-alkoxy, 1–4C-alkoxycarbonyl, 1–4C-alkylcarbonyloxy, 1–4C-alkylcarbonyl, 1–4C-alkoxycarbonylamino or completely or predominantly fluorine-substituted 1–4C-alkoxy, and R7 is hydroxyl, halogen, nitro, 1–4C-alkyl or 1–4C-alkoxy, and the salts, the N-oxides and the salts of the N-oxides of these compounds.

Compounds of the formula I of embodiment A to be emphasized are those in which

R1 is 1–2C-alkoxy, 3–5C-cycloalkoxy, 3–5C-cycloalkylmethoxy or completely or predominantly fluorine-substituted 1–2C-alkoxy, R2 is 1–2C-alkoxy, 3–5C-cycloalkoxy, 3–5C-cycloalkylmethoxy or completely or predominantly fluorine-substituted 1–2C-alkoxy, R3 is hydrogen,
R31 is hydrogen,
R4 is hydrogen or 1–2C-alkyl,
R5 is hydrogen,
R51 is hydrogen,
or in which
R5 and R51 together represent an additional bond,
Het is an unsubstituted or R6- and/or R7-substituted radical selected from the group consisting of benzofuran-2-yl, benzofuran-3-yl, 2,3-dihydrobenzofuran-2-yl, 2,3-dihydrobenzofuran-3-yl, chroman-2-yl, chroman-3-yl, chroman-4-yl, isochroman-1-yl, 1,4-benzodioxan-2-yl, 1,3-benzodioxol-2-yl, quinolin-2-yl, quinolin-4-yl, quinolin-3-yl, isoquinolin-3-yl, isoquinolin-1-yl, isoquinolin-4-yl, 1,2,3,4-tetrahydroacridin-9-yl, acridin-9-yl, indolizin-2-yl, indolizin-3-yl, indolizin-5-yl, indolizin-6-yl, indolizin-7-yl, indolizin-8-yl, phenanthridin-6-yl, cinnolin-3-yl, cinnolin-4-yl, quinazolin-4-yl, quinoxalin-2-yl, phthalazin-1-yl, 1,7-naphthyridin-3-yl, 1,6-naphthyridin-3-yl, 1,6-naphthyridin-4-yl, 1,6-naphthyridin-5-yl, 1,5-naphthyridin-2-yl, 1,5-naphthyridin-3-yl, 1,5-naphthyridin-4-yl, 1,5-naphthyridin-6-yl, 1,5-naphthyridin-7-yl, 1,5-naphthyridin-8-yl, indol-3-yl, indol-2-yl, indazol-3-yl, benzimidazol-2-yl, 2,3-dihydro-1H-indol-2-yl, 2,3-dihydro-1H-indol-3-yl, 2,3-dihydro-1H-isoindol-1-yl, 2,3-dihydro-1H-isoindol-3-yl, 1,2,3,4-tetrahydroquinolin-2-yl, 1,2,3,4-tetrahydroquinolin-3-yl, 1,2,3,4-tetrahydroquinolin-4-yl, 1,2,3,4-tetrahydroisoquinolin-1-yl, 1,2,3,4-tetrahydroisoquinolin-3-yl, 1,2,3,4-tetrahydroisoquinolin-4-yl, β-carbolin-1-yl, β-carbolin-3-yl, β-carbolin-4-yl, pyrimidin-4-yl, pyrimidin-5-yl, pyrimidin-2-yl, pyridazin-4-yl, pyridazin-3-yl and pyrazin-2-yl, where
R6 is hydroxyl, halogen, nitro, amino, aminocarbonyl, 1–4C-alkyl, 1–4C-alkoxy, 1–4C-alkylcarbonyl 1–4C-alkoxycarbonyl or completely or predominantly fluorine-substituted 1–2C-alkoxy, and
R7 is hydroxyl, halogen, 1–4C-alkyl or 1–4C-alkoxy, and the salts, the N-oxides and the salts of the N-oxides of these compounds.

The compounds of the formula I are chiral compounds having chiral centers in positions 4a and 10b and, depending on the meaning of the substituents R3, R31, R4, R5 and R51, further chiral centers in the positions 1, 2, 3 and 4.
Numbering:

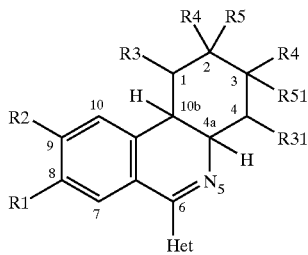

(I)

The invention therefore comprises all conceivable pure diastereomers and pure enantiomers and their mixtures in any mixing ratio, including the racemates. The compounds of the formula I are preferred in which the hydrogen atoms in positions 4a and 10b are cis to one another. The pure cis enantiomers are particularly preferred.

In this connection, particularly preferred compounds of the formula I are those in which positions 4a and 10b have the same absolute configuration as the compound (−)-cis-1,2-dimethoxy-4-(2-aminocyclohexyl)benzene employable as a starting compound and having the optical rotation $$[\alpha]_D^{20} = -58.5° \ (c = 1, \text{ethanol}).$$

The enantiomers can be separated in a manner known per se (for example by preparation and separation of appropriate diastereoisomeric compounds). Preferably, an enantiomer separation is carried out at the stage of the starting compounds of the formula IV

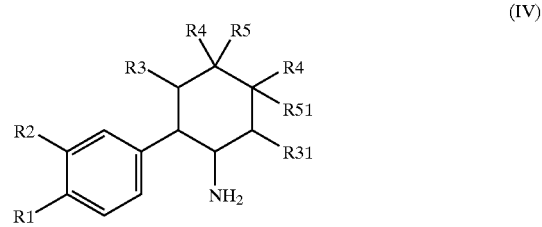

(IV)

for example by means of salt formation of the racemic compounds of the formula IV with optically active carboxylic acids. Examples which may be mentioned in this connection are the enantiomeric forms of mandelic acid, tartaric acid, O,O'-dibenzoyltartaric acid, camphoric acid, quinic acid, glutamic acid, malic acid, camphorsulfonic acid, 3-bromocamphorsulfonic acid, α-methoxyphenylacetic acid, α-methoxy-α-trifluoromethylphenylacetic acid and 2-phenylpropionic acid. Alternatively, enantiomerically pure starting compounds of the formula IV can also be prepared via asymmetric syntheses.

The preparation of the compounds of the formula I in which R1, R2, R3, R31, R4, R5, R51 and Het have the meanings indicated above and their salts can be carried out, for example, by the process described below in greater detail.

The process comprises cyclocondensing compounds of the formula II

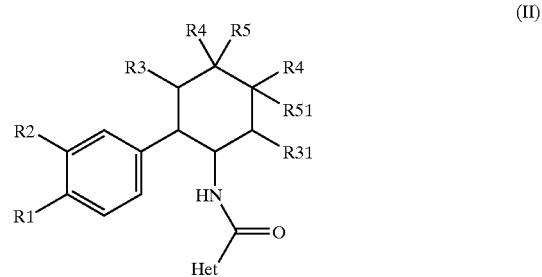

(II)

in which R1, R2, R3, R31, R4, R5, R51 and Het have the meanings indicated above, and if desired then converting the compounds of the formula I obtained into their salts, or by, if desired, then converting salts of the compounds of the formula I obtained into the free compounds.

Compounds of the formula I obtained can, if desired, be converted into further compounds of the formula I by derivatization.

For example, starting from compounds of the formula I in which a) R6 is an ester group, the corresponding amides can be prepared by reaction with suitably substituted amines;

b) R6 is a 1–4C-alkylcarbonyloxy group, the corresponding hydroxy compounds can be obtained by acidic or alkaline hydrolysis;

c) R6 and/or R7 is a nitro group, the corresponding amino compounds, which for their part can be further derivatized, are obtained by selective catalytic hydrogenation of the corresponding amino compounds.

The methods mentioned under a), b) and c) are expediently carried out analogously to the methods known to the person skilled in the art.

In addition, the compounds of the formula I can be converted, if desired, into their N-oxides, for example with the aid of hydrogen peroxide in methanol or the aid of m-chloroperoxybenzoic acid in dichloromethane. The person skilled in the art is familiar on the basis of his/her expert knowledge with reaction conditions which are specifically necessary for carrying out the N-oxidation.

The cyclocondensation is carried out in a manner known per se to the person skilled in the art according to Bischler-Napieralski (e.g. as described in J. Chem. Soc., 1956, 4280–4282) in the presence of a suitable condensing agent, such as polyphosphoric acid, phosphorus pentachloride, phosphorus pentoxide or preferably phosphorus oxychloride, in a suitable inert solvent, e.g. in a chlorinated hydrocarbon such as chloroform, or in a cyclic hydrocarbon such as toluene or xylene, or another inert solvent such as acetonitrile, or without further solvent using an excess of condensing agent, preferably at elevated temperature, in particular at the boiling temperature of the solvent or condensing agent used.

Compounds of the formula II in which R1, R2, R3, R31, R4, R5, R51 and Het have the meanings indicated above are accessible by reaction of the compounds of the formula IV in which R1, R2, R3, R31, R4, R5 and R51 have the meanings indicated above with compounds of the formula III

(III)

in which Het has the meanings indicated above and X is a suitable leaving group, preferably a chlorine atom. For example, the acylation or benzoylation is carried out as described in the following examples or as in J. Chem. Soc. (C), 1971, 1805–1808.

Alternatively to the process described above, compounds of the formula II in which R1, R2, R3, R31, R4, R5, R51 and Het have the meanings indicated above can also be prepared from the corresponding compounds of the formula IV in which R1, R2, R3, R31, R4, R5 and R51 have the meanings indicated above and compounds of the formula III in which Het has the meanings indicated above and X is hydroxyl, by reaction with amide bond linking reagents known to the person skilled in the art. Exemplary amide bond linking reagents known to the person skilled in the art which may be mentioned are, for example, the carbodiimides (e.g. dicyclohexylcarbodiimide), azodicarboxylic acid derivatives (e.g. diethyl azodicarboxylate), uronium salts [e.g. O-(benzotriazol-1-yl)-N,N,N',N'-tetramethyluronium tetrafluoroborate] and N,N'-carbonyldiimidazole.

This alternative preparation process is particularly suitable for the preparation of compounds of the formula II in which Het is substituted by amino or hydroxyl substituents or in which Het represents a condensed bi- or tricyclic ring system comprising at least one aromatic ring and one NH group.

Compounds of the formula III and compounds of the formula IV are either known or can be prepared in a known manner.

The compounds of the formula IV can be prepared, for example, from compounds of the formula V,

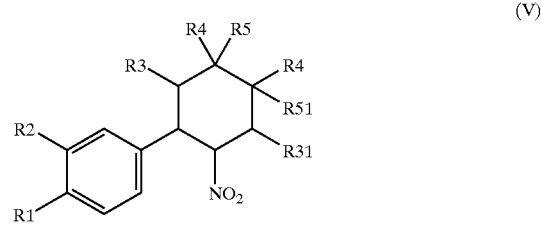

(V)

in which R1, R2, R3, R31, R4, R5 and R51 have the abovementioned meanings, by reduction of the nitro group.

The reduction is carried out in a manner known to the person skilled in the art, for example as described in J. Org. Chem. 1962, 27, 4426 or as described in the following examples.

The reduction can be carried out, for example, by catalytic hydrogenation, e.g. in the presence of Raney nickel, in a lower alcohol such as methanol or ethanol at room temperature and under normal or elevated pressure. If desired, a catalytic amount of an acid, such as, for example, hydrochloric acid, can be added to the solvent. Preferably, however, the reduction is carried out using metals such as zinc or iron with organic acids such as acetic acid or mineral acids such as hydrochloric acid.

The compounds of the formula IV in which R1, R2, R3, R31 and R4 have the meanings indicated above and R5 and R51 together represent an additional bond can be prepared from the corresponding compounds of the formula V by selective reduction of the nitro group in a manner known to the person skilled in the art, for example in the presence of Raney nickel in a lower alcohol as solvent using hydrazine hydrate as a hydrogen donor.

The compounds of the formula V, in which R1, R2, R3, R31 and R4 have the meanings indicated above and R5 and R51 are hydrogen, are either known or can be prepared from corresponding compounds of the formula V in which R5 and R51 together are an additional bond. The reaction can be carried out in a manner known to the person skilled in the art, preferably by hydrogenation in the presence of a catalyst, such as, for example, palladium on active carbon, e.g. as described in J. Chem. Soc. (C), 1971, 1805–1808.

The compounds of the formula V, in which R5 and R51 together are an additional bond, are either known or can be obtained by the reaction of compounds of the formula VI,

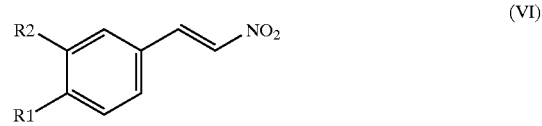

(VI)

in which R1 and R2 have the meanings mentioned above, with compounds of the formula VII,

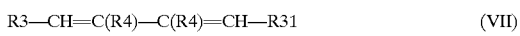

R3—CH=C(R4)—C(R4)=CH—R31          (VII)

in which R3, R31 and R4 have the meanings mentioned above.

Compounds of the formula V in which R5 and R51 are together an additional bond and R3 and R31 are together a 1–4C-alkylene group can be obtained, for example, by reaction of cyclic compounds of the formula VII, in which R4 has the meanings indicated above and R3 and R31 together are a 1–4C-alkylene group [e.g. cyclohexa-1,3-diene, 2,3-dimethylcyclohexa-1,3-diene, cyclohepta-1,3-diene, 2,3-dimethylcyclohepta-1,3-diene or cycloocta-1,3-diene], with compounds of the formula VI in which R1 and R2 have the abovementioned meanings.

The cycloaddition is in this case carried out in a manner known to the person skilled in the art according to Diels-Alder, e.g. as described in J. Amer. Chem. Soc. 1957, 79, 6559 or in J. Org. Chem. 1952, 17, 581 or as described in the following examples.

Compounds of the formula V obtained in the cycloaddition, in which the phenyl ring and the nitro group are trans to one another, can be converted in a manner known to the person skilled in the art into the corresponding cis compounds, e.g. as described in J. Amer. Chem. Soc. 1957, 79, 6559 or as described in the following examples.

The compounds of the formulae VI and VII are either known or can be prepared in a known manner. The compounds of the formula VI can be prepared, for example, in a manner known to the person skilled in the art from corresponding compounds of the formula VIII as described, for example, in J. Chem. Soc. 1951, 2524 or in J. Org. Chem. 1944, 9, 170 or as described in the following examples.

The compounds of the formula VIII,

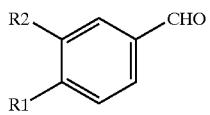

(VIII)

in which R1 and R2 have the meanings indicated above, are either known or can be prepared in a manner known to the person skilled in the art, as described, for example, in Ber. Dtsch. Chem. Ges. 1925, 58, 203.

It is known to the person skilled in the art that in the case of a number of reactive centers on a starting or intermediate compound it may be necessary to block one or more reactive centers temporarily by protective groups in order to allow a reaction to proceed specifically at the desired reaction center. A detailed description of the use of a large number of proven protective groups is found, for example, in T. W. Greene, Protective Groups in Organic Synthesis, John Wiley & Sons, 1991.

The isolation and purification of the substances according to the invention is carried out in a manner known per se, e.g. by distilling off the solvent in vacuo and recrystallizing the resulting residue from a suitable solvent or subjecting it to one of the customary purification methods, such as, for example, column chromatography on suitable support material.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low molecular weight aliphatic alcohol such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted by alkalization or by acidification into the free compounds, which in turn can be converted into salts. In this way, pharmacologically intolerable salts can be converted into pharmacologically tolerable salts.

The following examples serve to illustrate the invention further without restricting it. Likewise, further compounds of the formula I, whose preparation is not explicitly described, can be prepared in an analogous manner or in a manner familiar per se to the person skilled in the art using customary process techniques.

In the examples, m.p stands for melting point, h for hour(s), RT for room temperature, EF for empirical formula, MW for molecular weight, calc. for calculated and fnd. for found. The compounds mentioned in the examples and their salts are a preferred subject of the invention.

MS-method: EI-MS; Electron impact ionisation MS.

| HPLC-Method: | |
|---|---|
| Column: | Superspher 60 RP-select B (Merck) 75 × 4 mm |
| Column-temperature: | 40° C. |
| Solvent System: | A: Water (+0.5% Trifluoroacetic acid) |
| | B: Acetonitrile (+0.5% Trifluoroacetic acid) |

| Course of gradient: | | |
|---|---|---|
| min | % A | % B |
| 0.0 | 80 | 20 |
| 1.0 | 80 | 20 |
| 7.0 | 25 | 75 |
| 10.0 | 25 | 75 |
| 12.0 | 80 | 20 |
| 14.0 | 80 | 20 |

| Flow: | 1 ml/min |
|---|---|
| Detection: | UV (254 nm) |

EXAMPLES

Final Products 1. (−)-cis-8,9-Dimethoxy-6-quinolin-4-yl-1,2,3,4,4a,10b-hexahydrophenanthridine A solution of 4.0 g of (−)-cis-N-[2-(3,4-dimethoxyphenyl)cyclohexyl]quinoline-4-carboxamide (compound A1) in 30 ml of acetonitrile is added dropwise at RT in the course of 30 min to 10 g of phosphorus pentachloride in 20 ml of acetonitrile. After stirring at RT for 3 h, the mixture is diluted with ethyl acetate and hydrolyzed by addition of water. The organic phase is extracted with 1N sodium hydroxide solution and water, dried using sodium sulfate and then concentrated under reduced pressure. The residue is chromatographed on silica gel using petroleum ether/ethyl acetate/triethylamine in the ratio 5/4/1.

MS: calc.: $C_{24}H_{24}N_2O_2$ (372.42); found: [M+1] 373.3

Specific rotation:

$$[\alpha]_D^{20} = -87.5° \ (c = 0.2; DMF)$$

2. cis-8,9-Dimethoxy-6-(1-methyl-1H-pyrrol-2-yl)-1,2,3,4,4a,10b-hexahydrophenanthridine To a solution of 44.83 mg furan-2-carboxylic acid in 2800 µl dichloromethane 94 mg (−)-cis-1,2-dimethoxy-4-(2-aminocyclohexyl)benzene (compound B2) and 92 mg N-dimethylaminoethyl-N'-ethyl-carbodiimide are added and the resulting mixture is stirred for 16 h at RT. The reaction mixture is put on a cartidge loaded with 3 g silica and 3 g aluminium oxide neutral and eluted with ethyl acetate. The filtrate is evaporated to dryness and dissolved again in 1600 µl acetonitrile. To this solution 100 mg phosphorus pentachloride are added and the resulting mixture is stirred for 16 h at RT, after which 900 µl of a sodium hydroxide solution (10%) are added. After stirring for further 2 h at RT, the reaction mixture is evaporated to dryness and the title compound is purified by flash chromatography.

MS: calc: $C_{20}H_{24}N_2O_2$ (324.43): found: [M+1]: 325.4

The following examples are prepared analogously to compound 2:

3. cis-8,9-Dimethoxy-6-(5-methyl-3-phenyl-isoxazo-4-yl-1,2,3,4,4a, 10b-hexahydrophenanthridine MS: calc: $C_{25}H_{26}N_2O_3$ (402.50): found: [M+1]: 403.3

4. cis8,9-Dimethoxy-6-(furan-2-yl)-1,2,3,4,4a,10 b-hexahydrophenanthridine

MS: calc: $C_{19}H_{21}NO_3$ (311.38): found: [M+1]: 312.3 HPLC [min]: 5.36

5. cis-8,9-Dimethoxy-6-(1H-pyrrol-2yl)-1,2,3,4,4a,10b-hexahydrophenanthridine

MS: calc: $C_{19}H_{22}N_2O_2$ (310.40): found: [M+1]: 311.3

6. cis-8,9-Dimethoxy-6-(furan-3-yl)-1,2,3,4,4a,10b-hexahydrophenanthridine

MS: calc: $C_{19}H_{21}NO_3$ (311.38): found: [M+1]: 312.3 HPLC [min]: 5.44

7. cis-8,9-Dimethoxy-6-(thiophen-2-yl)-1,2,3,4,4a,10b-hexahydrophenanthridine

MS: calc: $C_{19}H_{21}NO_2S$ (327.45): found: [M+1]: 328.3 HPLC [min]: 5.73

8. cis-8,9-Dimethoxy-6-(5-methyl-thiophen-2-yl)-1,2,3,4,4a,10b-hexahydrophenanthridine MS: calc: $C_{20}H_{23}NO_2S$ (341.48): found: [M+1]: 342.3

9. cis-8,9-Dimethoxy-6-(thiophen-3-yl)-1,2,3,4,4a,10b-hexahydrophenanthridine

MS: calc: $C_{19}H_{21}NO_2S$ (327.45): found: [M+1]: 328.3 HPLC [min]: 5.73

10. cis-8,9-Dimethoxy-6-(1H-indol-2-yl)-1,2,3,4,4a,10b-hexahydrophenanthridine trifluoroacetate MS: calc: $C_{25}H_{25}F_3N_2O_4$ (360.46): found: [M+1]: 361.3

11. cis-8,9-Dimethoxy-6-(5-fluoro-1H-indol-2-yl)-1,2,3,4,4a,10b-hexahydrophenanthridine trifluoroacetate MS: calc: $C25H_{24}F_4N_2O_4$ (378.45): found: [M+1]: 379.4

12. cis-8,9-Dimethoxy-6-(6-methoxy-1H-indol-2-yl)-1,2,3,4,4a,10b-hexahydrophenanthridine trifluoroacetate MS: calc: $C_{26}H_{27}F_3N_2O_5$ (390.49): found: [M+1]: 391.4

13. cis-8,9-Dimethoxy-6-(benzofuran-2-yl)-1,2,3,4,4a,10b-hexahydr phenanthridine MS: calc: $C_{23}H_{23}NO_3$ (361.44): found: [M+1]: 362.3

14. cis-8,9-Dimethoxy-6-(pyrazin-2-yl)-1,2,3,4,4a,10b-hexahydrophenanthridine

MS: calc: $C_{19}H_{21}N_3O_2$ (323.40): found: [M+1]: 324.3

15. cis-8,9-Dimethoxy-6-(quinolin-2-yl)-1,2,3,4,4a,10b-hexahydrophenanthridine

MS: calc: $C_{24}H_{24}N_2O_2$ (372.47): found: [M+1]: 373.3 HPLC [min]: 6.32

16. cis-8,9-Dimethoxy-6-(3-methyl-furan-2-yl)-1,2,3,4,4a, 10b-hexahydrophenanthridine MS: calc: $C_{20}H_{23}NO_3$ (325.41): found: [M+1]: 326.3

17. cis-8,9-Dimethoxy-6-(benzo[b]thiophen-2-yl)-1,2,3,4,4a,10b-hexahydrophenanthridine MS: calc: $C_{23}H_{23}NO_2S$ (377.51): found: [M+1]: 378.3

18. cis-8,9-Dimethoxy-6-(3,5-dimethyl-isoxazol-4-yl)-1,2,3,4,4a,10b-hexahydrophenanthridine MS: calc: $C_{20}H_{24}N_2O_3$ (340.43): found: [M+1]: 341.3

19. cis-8,9-Dimethoxy-6-(4-phenyl-[1,2,3]thiadiazol-5-yl)-1,2,3,4,4a, 10b-hexahydrophenanthridine MS: calc: $C_{23}H_{23}N_3O_2S$ (405.52): found: [M+1]: 406.0

20. cis-8,9-Dimethoxy-6-(3-methyl-benzofuran-2-yl)-1,2,3,4,4a,10b-hexahydrophenanthridine MS: calc: $C_{24}H_{25}NO_3$ (375.47): found: [M+1]: 376.3 HPLC [min]: 6.80

21. cis-8,9-Dimethoxy-6-(7-methoxy-benzofuran-2-yl)-1,2,3,4,4a,10b-hexahydrophenanthridine MS: calc: $C_{24}H_{25}NO_4$ (391.47): found: [M+1]: 392.3 HPLC [min]: 6.75

22. cis-8,9-Dimethoxy-6-(5-methyl-pyrazin-2-yl)-1,2,3,4,4a,10b-hexahydrophenanthridine MS: calc: $C_{20}H_{23}N_3O_2$ (337.43): found: [M+1]: 338.3

23. cis-8,9-Dimethoxy-6-(5-methoxy-benzofuran-2-yl)-1,2,3,4,4a,10b-hexahydrophenanthridine MS: calc: $C_{24}H_{25}NO_4$ (391.47): found: [M+1]: 392.3 HPLC [min]: 6.75

24. cis-8,9-Dimethoxy-6-(1,5-dimethyl-1H-pyrazol-3-yl)-1,2,3,4,4a, 10b-hexahydrophenanthridine MS: calc: $C_{20}H_{25}N_3O_2$ (339.44): found: [M+1]: 340.4

25. cis-8,9-Dimethoxy-6-(4-methyl-[1,2,3]thiadiazol-5-yl)-1,2,3,4,4a, 10b-hexahydrophenanthridine MS: calc: $C_{18}H_{21}N_3O_2S$ (343.45): found: [M+1]: 344.1

26. cis-8,9-Dimethoxy-6-(isoxazol-5-yl)-1,2,3,4,4a,10b-hexahydrophenanthridine

MS: calc: $C_{18}H_{20}N_2O_3$ (312.37): found: [M+1]: 313.3

27. cis-8,9-Dimethoxy-6-(isoquinolin-1-yl)-1,2,3,4,4a,10b-hexahydrophenanthridine MS: calc: $C_{24}H_{24}N_2O_2$ (372.47): found: [M+1]: 373.4 HPLC [min]: 5.92

Starting Compounds

A1. (−)-cis-N-[2-(3,4-Dimethoxyphenyl)cyclohexyl]-quinoline-4-carboxamide 4.0 g of (−)-cis-1,2-dimethoxy-4-(2-aminocyclohexyl) benzene (compound B2) are dissolved in 50 ml of dichloromethane and 10 ml of triethylamine. A solution of 3.9 g of 4-quinoline carbonyl chloride in 50 ml of dichloromethane is added dropwise at RT, and the mixture is extracted after stirring overnight with 100 ml each of water, 2N hydrochloric acid, satd. sodium hydrogencarbonate solution and water again. The organic phase is dried using sodium sulfate and concentrated and the residue is crystallized from ethyl acetate/petroleum ether.

M.p.: 149–152° C.

Specific rotation:

$$[\alpha]_D^{20} = -29.5° \; (c = 0.2 \text{ ethanol})$$

B1. (+/−)-cis-1,2-Dimethoxy-4-(2-aminocyclohexyl) benzene 125 g of (+/−)-cis-1,2-dimethoxy-4-(2-nitrocyclohexyl) benzene and 120 g of zinc powder or granules are suspended in 1300 ml of ethanol. 220 ml of acetic acid are added dropwise at boiling heat. The precipitate is filtered off with suction and washed with ethanol, and the filtrate is concentrated under reduced pressure. The residue is taken up in hydrochloric acid and extracted with toluene. The aqueous phase is rendered alkaline using 50% strength sodium hydroxide solution, the precipitate is filtered off with suction and the filtrate is extracted with toluene. The organic phase is dried using sodium sulfate and concentrated. 98 g of the title compound are obtained as a crystallizing oil.

Alternatively:

8.5 g of (+/−)-cis-1,2-dimethoxy-4-(2-nitrocyclohexyl) benzene are dissolved in 400 ml of methanol and treated at RT with 7 ml of hydrazine hydrate and 2.5 g of Raney nickel in portions in the course of 8 h. After stirring overnight at RT, the reaction mixture is filtered, the filtrate is concentrated and the residue is chromatographed on silica gel using a mixture of toluene/ethyl acetate/triethylamine=4/2/0.5. The title compound is obtained as an oil.

B2. (−)-cis-1,2-Dimethoxy-4-(2-aminocyclohexyl)benzene 12.0 g of (+/−)-cis-1,2-dimethoxy-4-(2-aminocyclohexyl) benzene and 6.2 g of (−)-mandelic acid are dissolve in 420 ml of dioxane and 60 ml of tetrahydrofuran and the solution is stirred overnight at RT. The solid is filtered off with suction, dried, treated with 100 ml of saturated sodium hydrogencarbonate solution and extracted with ethyl acetate. The organic phase is dried using sodium sulfate and concentrated under reduced pressure. 4.8 g of the title compound are obtained of m.p.: 80–81.5° C.

Specific rotation:

$$[\alpha]_D^{20} = -58.5°C \ (c = 1, \text{ethanol}).$$

C1. (+/−)-cis-1,2-Dimethoxy-4-(2-nitrocyclohex-4-enyl)benzene 10.0 g of (+/−)-trans-1,2-dimethoxy-4-(2-nitrocyclohex-4-enyl)benzene and 20.0 g of potassium hydroxide are dissolved in 150 ml of ethanol and 35 ml of dimethylformamide. A solution of 17.5 ml of conc. sulfuric acid in 60 ml of ethanol is then added dropwise such that the internal temperature does not exceed 4° C. After stirring for 1 h, the mixture is added to 1 l of ice water, the precipitate is filtered off with suction, washed with water and dried, and the crude product is recrystallized from ethanol. 8.6 g of the title compound of m. p. 82.5–84° C. are obtained.

C2. (+/−)-cis-1,2-Dimethoxy-4-(2-nitrocyclohexyl)benzene 8.4 g of (+/−)-cis-1,2-dimethoxy-4-(2-nitrocyclohex-4-enyl)benzene are dissolved in 450 ml of methanol, treated with 2 ml of conc. hydrochloric acid and hydrogenated after addition of 500 mg of 10% strength Pd/C. The reaction mixture is filtered and the filtrate is concentrated. M.p.: 84–86.5° C.

D1. (+/−)-trans-1,2-Dimethoxy-4-(2-nitrocyclohex-4-enyl)benzene 50.0 g of 3,4-dimethoxy-ω-nitrostyrene and 1.0 g (9.1 mmol) of hydroquinone are suspended in 200 ml of abs. toluene and treated at −70° C. with 55.0 g (1.02 mol) of liquid 1,3-butadiene. The mixture is stirred at 160° C. for 6 days in an autoclave and then cooled. Some of the solvent is removed on a rotary evaporator, and the resulting precipitate is filtered off with suction and recrystallized in ethanol. M.p.: 113.5–115.5° C.

E1. 3,4-Dimethoxy-ω-nitrostyrene 207.0 g of 3,4-dimethoxybenzaldehyde, 100.0 g of ammonium acetate and 125 ml of nitromethane are heated to boiling for 3–4 h in 1.0 l of glacial acetic acid. After cooling in an ice bath, the precipitate is filtered off with suction, rinsed with glacial acetic acid and petroleum ether and dried. M.p.: 140–141° C. Yield: 179.0 g.

Commercial Applicability

The compounds according to the invention have valuable pharmacological properties which make them commercially utilizable. As selective cyclic nucleotide phosphodiesterase (PDE) inhibitors (namely of type 4), they are suitable on the one hand as bronchial therapeutics (for the treatment of airway obstructions on account of their dilating but also on account of their respiratory rate—or respiratory drive-increasing action) and for the elimination of erectile dysfunction on account of the vasodilating action, but on the other hand especially for the treatment of disorders, in particular of inflammatory nature, e.g. of the airways (asthma prophylaxis), of the skin, of the central nervous system, of the intestine, of the eyes and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen radicals and proteases. The compounds according to the invention are distinguished here by low toxicity, good enteral absorption (high bioavailability), a large therapeutic breadth and the absence of significant side-effects.

On account of their PDE-inhibiting properties, the compounds according to the invention can be employed in human and veterinary medicine and therapeutics, where they can be used, for example, for the treatment and prophylaxis of the following illnesses: acute and chronic (in particular inflammatory and allergen-induced) airway disorders of various origins (bronchitis, allergic bronchitis, bronchial asthma, emphysema, COPD); dermatoses (especially of proliferative, inflammatory and allergic type) such as, for example, psoriasis (vulgaris), toxic and allergic contact eczema, atopic eczema, seborrheic eczema, lichen simplex, sunburn, pruritus in the anogenital area, alopecia areata, hypertrophic scars, discoid lupus erythematosus, follicular and wide-area pyodermias, endogenous and exogenous acne, acne rosacea and other proliferative, inflammatory and allergic skin disorders; disorders which are based on an excessive release of TNF and leukotrienes, e.g. disorders of the arthritis type (rheumatoid arthritis, rheumatoid spondylitis, osteoarthritis and other arthritic conditions), disorders of the immune system (AIDS, multiple sclerosis), graft-versus-host reactions, transplant rejection reactions, symptoms of shock [septic shock, endotoxin shock, gram-negative sepsis, toxic shock syndrome and ARDS (adult respiratory distress syndrome)], and generalized inflammations in the gastrointestinal area (Crohn's disease and ulcerative colitis); disorders which are based on allergic and/or chronic, faulty immunological reactions in the area of the upper airways (pharynx, nose) and the adjacent regions (paranasal sinuses, eyes), such as, for example, allergic rhinitis/sinusitis, chronic rhinitis/sinusitis, allergic conjunctivitis and nasal polyps; but also disorders of the heart which can be treated by PDE inhibitors, such as, for example, cardiac insufficiency, or disorders which can be treated on account of the tissue-relaxant action of the PDE inhibitors, such as, for example, erectile dysfunction or colics of the kidneys and the ureters in connection with kidney stones. In addition, the compounds according to the invention can be employed for the treatment of diabetes insipidus and disorders in connection with disturbances of brain metabolism, such as, for example, cerebral senility, senile dementia (Alzheimer's dementia), multiinfarct dementia or alternatively disorders of the CNS, such as, for example, depressions or arteriosclerotic dementia.

The invention further relates to the compounds according to the invention for use in the treatment of mammals, including man, which are suffering from one of the above-mentioned illnesses. The process comprises administering to the sick mammal a therapeutically efficacious and pharmacologically tolerable amount of one or more of the compounds according to the invention.

The invention further relates to the compounds according to the invention for use in the treatment and/or prophylaxis of illnesses, in particular the illnesses mentioned.

The invention likewise relates to the use of the compounds according to the invention for the production of medicaments which are employed for the treatment and/or prophylaxis of the illnesses mentioned.

Medicaments for the treatment and/or prophylaxis of the illnesses mentioned, which contain one or more of the compounds according to the invention, are furthermore a subject of the invention.

A further subject of the invention is a commercial product, consisting of a customary secondary pack, a primary pack containing the medicament (for example an ampoule or a blister pack) and, if desired, a pack insert, the medicament exhibiting antagonistic action against cyclic nucleotide phosphodiesterases of type 4 (PDE4) and leading to the attenuation of the symptoms of illnesses which are connected with cyclic nucleotide phosphodiesterases of type 4, and the suitability of the medicament for the prophylaxis or treatment of illnesses which are connected with cyclic nucleotide phosphodiesterases of type 4 being indicated on the secondary pack and/or on the pack insert of the commercial product, and the medicament containing one or more compounds of the formula I according to the invention. The secondary pack, the primary pack containing the medicament and the pack insert otherwise comply with what would be regarded as standard to the person skilled in the art for medicaments of this type.

The medicaments are prepared by processes which are known per se and familiar to the person skilled in the art. As medicaments, the compounds according to the invention (=active compounds) are either employed as such, or preferably in combination with suitable pharmaceutical excipients, e.g. in the form of tablets, coated tablets, capsules, suppositories, patches, emulsions, suspensions, gels or solutions, the active compound content advantageously being between 0.1 and 95%.

The person skilled in the art is familiar on the basis of his/her expert knowledge with the excipients which are suitable for the desired pharmaceutical formulations. In addition to solvents, gel-forming agents, ointment bases and other active compound vehicles, it is possible to use, for example, antioxidants, dispersants, emulsifiers, preservatives, solubilizers or permeation promoters.

For the treatment of disorders of the respiratory tract, the compounds according to the invention are preferably also administered by inhalation in the form of an aerosol; the aerosol particles of solid, liquid or mixed composition preferably having a diameter of 0.5 to 10 μm, advantagously of 2 to 6 μm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the compounds according to the invention are in particular used in the form of those medicaments which are suitable for topical application. For the production of the medicaments, the compounds according to the invention (=active compounds) are preferably mixed with suitable pharmaceutical excipients and further processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by processes known per se. Dosage of the active compounds takes place in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.1 and 3 mg per day. The customary dose in the case of systemic therapy (p.o. or i.v.) is between 0.03 and 3 mg per kilogram per day.

Bi logical Investigations

The second messenger cyclic AMP (cAMP) is well-known for inhibiting inflammatory and immunocompetent cells. The PDE4 isoenzyme is broadly expressed in cells involved in the initiation and propagation of inflammatory diseases (H Tenor and C Schudt, in "Phosphodiesterase Inhibitors", 21–40, "The Handbook of Immunopharmacology", Academic Press, 1996), and its inhibition leads to an increase of the intracellular cAMP concentration and thus to the inhibition of cellular activation (J E Souness et al., Immunopharmacology 47: 127–162, 2000).

The antiinflammatory potential of PDE4 inhibitors in vivo in various animal models has been described (M M Teixeira, TiPS 18: 164–170, 1997). For the investigation of PDE4 inhibition on the cellular level (in vitro), a large variety of proinflammatory responses can be measured. Examples are the superoxide production of neutrophilic (C Schudt et al., Arch Pharmacol 344: 682–690, 1991) or eosinophilic (A Hatzelmann et al., Brit J Pharmacol 114: 821–831, 1995) granulocytes, which can be measured as luminol-enhanced chemiluminescence, or the synthesis of tumor necrosis factor-α in monocytes, macrophages or dendritic cells (Gantner et al., Brit J Pharmacol 121: 221–231, 1997, and Pulmonary Pharmacol Therap 12: 377–386, 1999). In addition, the immunomodulatory potential of PDE4 inhibitors is evident from the inhibition of T-cell responses like cytokine synthesis or proliferation (D M Essayan, Biochem Pharmacol 57: 965–973, 1999). Substances which inhibit the secretion of the afore-mentioned proinflammatory mediators are those which inhibit PDE4. PDE4 inhibition by the compounds according to the invention is thus a central indicator for the suppression of inflammatory processes.

Method for Measuring Inhibition of PDE4 Activity

PDE4 activity was determined as described by Thompson et al. (Adv Cycl Nucl Res 10: 69–92, 1979) with some modifications (Bauer and Schwabe, Naunyn-Schmiedeberg's Arch Pharmacol 311: 193–198, 1980). At a final assay volume of 200 μl (96 well microtiter plates) the assay mixture contained 20 mM Tris (pH 7.4), 5 mM $MgCl_2$, 0.5 μM cAMP, [$^3$H]cAMP (about 30,000 cpm/assay), the test compound and an aliquot of cytosol from human neutrophils which mainly contains PDE4 activity as described by Schudt et al. (Naunyn-Schmiedeberg's Arch Pharmacol 344: 682–690, 1991); the PDE3-specific inhibitor Motapizone (1 μM) was included to suppress PDE3 activity originating from contaminating platelets. Serial dilutions of the compounds were prepared in DMSO and further diluted 1:100 (v/v) in the assays to obtain the desired final concentrations of the inhibitors at a DMSO concentration of 1% (v/v) which by itself only slightly affected PDE4 activity.

After preincubation for 5 min at 37° C., the reaction was started by the addition of substrate (cAMP) and the assays were incubated for further 15 min at 37° C. 50 μl of 0.2 N HCl was added to stop the reaction and the assays were left on ice for about 10 min. Following incubation with 25 μg 5'-nucleotidase (Crotalus atrox snake venom) for 10 min at 37° C., the assays were loaded on QAE Sephadex A-25 (1 ml bed volume). The columns were eluted with 2 ml of 30 mM ammonium formiate (pH 6.0) and the eluate was counted for radioactivity. Results were corrected for blank values (measured in the presence of denatured protein) which were below 5% of total radioactivity. The amount of cyclic nucleotides hydrolyzed did not exceed 30% of the original substrate concentration. The $IC_{50}$-values for the compounds according to the invention for the inhibition of the PDE4 activity were determined from the concentration-inhibition curves by nonlinear-regression.

The inhibitory values determined for the compounds according to the invention follow from the following table A, in which the numbers of the compounds correspond to the numbers of the examples.

TABLE A

Inhibition of PDE4 activity [measured as $-logC_{50}$ (mol/l)]

| Compound | $-logC_{50}$ |
|---|---|
| 1 | 7.4 |
| 7 | 8.14 |
| 8 | 8.19 |
| 9 | 7.45 |
| 10 | 8.19 |
| 11 | 8.14 |
| 12 | 8.27 |
| 15 | 7.68 |
| 16 | 7.42 |
| 17 | 8.84 |
| 20 | 8.53 |
| 21 | 8.51 |
| 23 | 8.33 |

What is claimed is:
1. A compound of formula I,

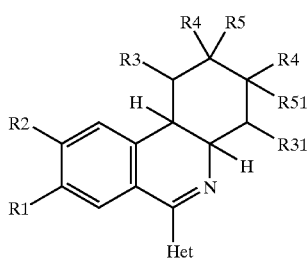

(I)

in which
R1 is hydroxyl, 1–4C-alkoxy, 3–7C-cycloalkoxy, 3–7C-cycloalkylmethoxy or completely or predominantly fluorine-substituted 1–4C-alkoxy,
R2 is hydroxyl, 1–4C-alkoxy, 3–7C-cycloalkoxy, 3–7C-cycloalkylmethoxy or completely or predominantly fluorine-substituted 1–4C-alkoxy,
or in which
R1 and R2 together are a 1–2C-alkylenedioxy group,
R3 is hydrogen or 1–4C-alkyl,
R31 is hydrogen or 1–4C-alkyl,
or in which
R3 and R31 together are a 1–4C-alkylene group,
R4 is hydrogen or 1–4C-alkyl,
R5 is hydrogen,
R51 is hydrogen,
or in which
R5 and R51 together represent an additional bond,
Het is an unsubstituted or R6- and/or R7-substituted radical selected from the group consisting of benzofuran-2-yl, benzofuran-3-yl, 2,3-dihydrobenzofuran-2-yl, 2,3-dihydrobenzofuran-3-yl, benzothiophen-2-yl, benzothiophen-3-yl, 2,3-dihydrobenzothiophen-2-yl, 2,3-dihydrobenzothiophen-3-yl, chroman-2-yl, chroman-3-yl, chroman-4-yl, isochroman-1-yl, 1,4-benzodioxan-2-yl, 1,3-benzodioxol-2-yl, quinolin-2-yl, quinolin-4-yl, quinolin-3-yl, isoquinolin-3-yl, isoquinolin-1-yl, isoquinolin-4-yl, 1,2,3,4-tetrahydroacridin-9-yl, acridin-9-yl, indolizin-2-yl, indolizin-3-yl, indolizin-5-yl, indolizin-6-yl, indolizin-7-yl, indolizin-8-yl, phenanthridin-6-yl, cinnolin-3-yl, cinnolin-4-yl, quinazolin-4-yl, quinoxalin-2-yl, phthalazin-1-yl, 1,7-naphthyridin-3-yl, 1,6-naphthyridin-3-yl, 1,6-naphthyridin-4-yl, 1,6-naphthyridin-5-yl, 1,5-naphthyridin-2-yl, 1,5-naphthyridin-3-yl, 1,5-naphthyridin-4-yl, 1,5-naphthyridin-6-yl, 1,5-naphthyridin-7-yl, 1,5-naphthyridin-8-yl, indol-3-yl, indol-2-yl, indazol-3-yl, benzimidazol-2-yl, 2,3-dihydro-1H-indol-2-yl, 2,3-dihydro-1H-indol-3-yl, 2,3-dihydro-1H-isoindol-1-yl, 2,3-dihydro-1H-isoindol-3-yl, 1,2,3,4-tetrahydroquinolin-2-yl, 1,2,3,4-tetrahydroquinolin-3-yl, 1,2,3,4-tetrahydroquinolin-4-yl, 1,2,3,4-tetrahydroisoquinolin-1-yl, 1,2,3,4-tetrahydroisoquinolin-3-yl, 1,2,3,4-tetrahydroisoquinolin-4-yl, β-carbolin-1-yl, β-carbolin-3-yl, β-carbolin-4-yl, furan-2-yl, furan-3-yl, thiophen-2-yl, thiophen-3-yl, 1H-pyrrol-2-yl, 1H-pyrrol-3-yl, pyrazol-3-yl, pyrazol-4-yl, imidazol-2-yl, imidazol-4-yl, imidazol-5-yl, oxazol-2-yl, oxazol-4-yl, oxazol-5-yl, thiazol-2-yl, thiazolyl-3-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, [1,2,3]thiadiazol-4-yl, [1,2,3]thiadiazol-5-yl, pyrimidin-4-yl, pyrimidin-5-yl, pyrimidin-2-yl, pyridazin-4-yl, pyridazin-3-yl and pyrazin-2-yl, where
R6 is hydroxyl, halogen, nitro, cyano, amino, aminocarbonyl, mono- or di-1–4C-alkylamino, mono- or di-1–4C-alkylaminocarbonyl, 1–4C-alkyl, trifluoromethyl, 1–4C-alkoxy, 1–4C-alkoxycarbonyl, 1–4C-alkylcarbonyloxy, 1–4C-alkylcarbonyl, 1–4C-alkoxycarbonylamino, phenyl or completely or predominantly fluorine-substituted 1–4C-alkoxy, and
R7 is hydroxyl, halogen, nitro, 1–4C-alkyl or 1–4C-alkoxy, or a hydrate, solvate, salt, hydrate of a salt, or solvate of a salt of that compound, or an N-oxide of that compound, or a hydrate, solvate, salt, hydrate of a salt or solvate of a salt thereof.
2. A compound of the formula I as claimed in claim 1, in which
R1 is 1–2C-alkoxy, 3–5C-cycloalkoxy, 3–5C-cycloalkylmethoxy or completely or predominantly fluorine-substituted 1–2C-alkoxy, R2 is 1–2C-alkoxy, 3–5C-cycloalkoxy, 3–5C-cycloalkylmethoxy or completely or predominantly fluorine-substituted 1–2C-alkoxy, R3 is hydrogen, R31 is hydrogen, R4 is hydrogen or 1–2C-alkyl, R5 is hydrogen, R51 is hydrogen, or in which R5 and R51 together represent an additional bond, Het is an unsubstituted or R6- and/or R7-substituted radical selected from the group consisting of benzofuran-2-yl, benzofuran-3-yl, 2,3-dihydrobenzofuran-2-yl, 2,3-dihydrobenzofuran-3-yl, benzothiophen-2-yl, benzothiophen-3-yl, 2,3-dihydrobenzothiophen-2-yl, 2,3-dihydrobenzothiophen-3-yl, chroman-2-yl, chroman-3-yl, chroman-4-yl, isochroman-1-yl, 1,4-benzodioxan-2-yl, 1,3-benzodioxol-2-yl, quinolin-2-yl, quinolin-4-yl, quinolin-3-yl, isoquinolin-3-yl, isoquinolin-1-yl, isoquinolin-4-yl, 1,2,3,4-tetrahydroacridin-9-yl, acridin-9-yl, indolizin-2-yl, indolizin-3-yl, indolizin-5-yl, indolizin-6-yl, indolizin-7-yl, indolizin-8-yl, phenanthridin-6-yl, cinnolin-3-yl, cinnolin-4-yl, quinazolin-4-yl, quinoxalin-2-yl, phthalazin-1-yl, 1,7-naphthyridin-3-yl, 1,6-naphthyridin-3-yl, 1,6-naphthyridin-4-yl, 1,6-naphthyridin-5-yl, 1,5-naphthyridin-2-yl, 1,5-naphthyridin-3-yl, 1,5-naphthyridin-4-yl, 1,5-naphthyridin-6-yl, 1,5-naphthyridin-7-yl, 1,5-naphthyridin-8-yl, indol-3-yl, indol-2-yl, indazol-3-yl, benzimidazol-2-yl, 2,3-dihydro-1H-indol-2-yl, 2,3-dihydro-1H-indol-3-yl, 2,3-dihydro-1H-isoindol-1-yl, 2,3-dihydro-1H-isoindol-3-yl, 1,2,3,4-tetrahydroquinolin-2-yl, 1,2,3,4-tetrahydroquinolin-3-yl, 1,2,3,4-tetrahydroquinolin-4-yl, 1,2,3,4-tetrahydroisoquinolin-1-yl, 1,2,3,4-tetrahydroisoquinolin-3-yl, 1,2,3,4-tetrahydroisoquinolin-4-yl, β-carbolin-1-yl, β-carbolin-3-yl, β-carbolin-4-yl, furan-2-yl, furan-3-yl, thiophen-2-yl, thiophen-3-yl, 1H-pyrrol-2-yl, 1H-pyrrol-3-yl, pyrazol-3-yl, pyrazol-4-yl, imidazol-2-yl, imidazol-4-yl, imidazol-5-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, [1,2,3]thiadiazol-4-yl, [1,2,3]thiadiazol-5-yl, pyrimidin-4-yl, pyrimidin-5-yl, pyrimidin-2-yl, pyridazin-4-yl, pyridazin-3-yl and pyrazin-2-yl, where R6 is hydroxyl, halogen, nitro, amino, aminocarbonyl, 1–4C-alkyl, 1–4C-alkoxy, 1–4C-alkylcarbonyloxy, 1–4C-alkoxycarbonyl or completely or predominantly fluorine-substituted 1–2C-alkoxy, and R7 is hydroxyl, halogen, 1–4C-alkyl or 1–4C-alkoxy, or a hydrate, solvate, salt, hydrate of a salt, or solvate of a salt of that compound, or an N-oxide of that compound, or a hydrate, solvate, salt, hydrate of a salt or solvate of a salt thereof.

3. A compound of the formula I as claimed in claim 1 in which

R1 is 1–2C-alkoxy,

R2 is 1–2C-alkoxy,

R3, R31, R4, R5 and R51 are hydrogen,

Het is an unsubstituted or R6- and/or R7-substituted radical selected from the group consisting of benzofuran-2-yl, benzothiophen-2-yl, quinolin-2-yl, quinolin-4-yl, isoquinolin-1-yl, indol-2-yl, furan-2-yl, furan-3-yl, thiophen-2-yl, thiophen-3-yl, 1H-pyrrol-2-yl, pyrazol-3-yl, thiazol-2-yl, thiazol-3-yl, isoxazol-4-yl, isoxazol-5-yl, [1,2,3]thiadiazol-5-yl and pyrazin-2-yl, where R6 is halogen, 1–4C-alkyl, 1–4C-alkoxy or phenyl, and R7 is 1–4C-alkyl, or a hydrate, solvate, salt, hydrate of a salt, or solvate of a salt of that compound, or an N-oxide of that compound, or a hydrate, solvate, salt, hydrate of a salt or solvate of a salt thereof.

4. A compound of the formula I as claimed in claim 1 in which

R1 is methoxy,

R2 is methoxy,

R3, R31, R4, R5 and R51 are hydrogen, and

Het is quinolin-4-yl, quinolin-2-yl, 3-methyl-furan-2-yl, 3-methyl-benzofuran-2-yl, 7-methoxy-benzofuran-2-yl, 5-methoxy-benzofuran-2-yl, thiophen-2-yl, 5-methyl-thiophen-2-yl, thiophen-3-yl, 1H-indol-2-yl, 5-fluoro-1H-indol-2-yl, 6-methoxy-1H-indol-2-yl, or a hydrate, solvate, salt, hydrate of a salt, or solvate of a salt of that compound, or an N-oxide of that compound, or a hydrate, solvate, salt, hydrate of a salt or solvate of a salt thereof.

5. A compound of the formula I as claimed in claim 1 in which

R1 is hydroxyl, 1–4C-alkoxy, 3–7C-cycloalkoxy, 3–7C-cycloalkylmethoxy or completely or predominantly fluorine-substituted 1–4C-alkoxy, R2 is hydroXyl, 1–4C-alkoxy, 3–7C-cycloalkoxy, 3–7C-cycloalkylmethoxy or completely or predominantly fluorine-substituted 1–4C-alkoxy, or in which R1 and R2 together are a 1–2C-alkylenedioxy group, R3 is hydrogen or 1–4C-alkyl, R31 is hydrogen or 1–4C-alkyl, or in which R3 and R31 together are a 1–4C-alkylene group, R4 is hydrogen or 1–4C-alkyl, R5 is hydrogen, R51 is hydrogen, or in which R5 and R51together represent an additional bond, Het is an unsubstituted or R6- and/or R7-substitUted radical selected from the group consisting of bezofuran-2-yl, benzofuran-3-yl, 2,3-dihydrobenzofuran-2-yl, 2,3-dihydrobenzofuran-3-yl, chroman-2-yl, chroman-3-yl, chroman-4-yl, isochroman-1-yl, 1,4-benzodioxan-2-yl, 1,3-benzodioxol-2-yl, quinolin-2-yl, quinolin-4-yl, quinolin-3-yl, isoquinolin-3-yl, isoquinolin-1-yl, isoquinolin-4-yl, 1,2,3,4-tetrahdroacridinyl-9-yl, acridinyl-9-yl, indolizin-2-yl, indolizin-3-yl, indolizin-5-yl, indolizin-6-yl, indolizin-7-yl, indolizin-8-yl, phenanthridin-6-yl, cinnolin-3-yl, cinnolin-4-yl, quinazolin-4-yl, quinoxalin-2-yl, phthalazin-1-yl, 1,7-naphthyridine-3-yl, 1,6-naphthyridin-3-yl, 1,6-naphthyridin-4-yl, 1,6-naphthyridin-5-yl, 1,5-naphthyridin-2-yl, 1,5-naphthyridin-3-yl, 1,5-naphthyridin-4-yl, 1,5-naphthyridin-6-yl, 1,5-naphthyridin-7-yl, 1,5-naphthyridin-8-yl, indol-2-yl, indol-3-yl, indazol-3-yl, benzimidazol-2-yl, 2,3-dihydro-1H-indol-2-yl, 2,3-dihydro-1H-indol-3-yl, 2,3-dihydro-1H-isoindol-1-yl, 2,3-dihydro-1H-isoindol-3-yl, 1,2,3,4-tetrahydroquinolin-2-yl, 1,2,3,4-tetrahydroquinolin-3-yl, 1,2,3,4-tetrahydroquinolin-4-yl, 1,2,3,4-tetrahydroisoquinolin-1-yl, 1,2,3,4-tetrahydroisoquinolin-3-yl, 1,2,3,4-tetrahydroisoquinolin-4-yl, β-carbolin-1-yl, β-carbolin-3-yl, β-carbolin-4-yl, pyrimidin-4-yl, pyrimidin-5-yl, pyrimidin-2-yl, pyridazin-4-yl, pyridazin-3-yl and pyrazin-2-yl, where R6 is hydroxyl, halogen, nitro, cyano, amino, aminocarbonyl, mono- or di-1–4C-alkylamino, mono- or di-1–4C-alkylaminocarbonyl 1–4C-alkyl, trifluoromethyl, 1–4C-alkoxy, 1–4C-alkoxycarbonyl, 1–4C-alkylcarbonyloxy, 1–4C-alkylcarbonyl, 1–4C-alkoxycarbonylamino or completely or predominantly fluorine-substituted 1–4C-alkoxy, and R7 is hydroxyl, halogen, nitro, 1–4C-alkyl or 1–4C-alkoxy, or a hydrate, solvate, salt, hydrate of a salt, or solvate of a salt of that compound, or an N-oxide of that compound, or a hydrate, solvate, salt, hydrate of a salt or solvate of a salt thereof.

6. A compound of the formula I as claimed in claim 1, in which

R1 is 1–2C-alkoxy, 3–5C-cycloalkoxy, 3–5C-cycloalkylmethoxy or completely or predominantly fluorine-substituted 1–2C-alkoxy, R2 is 1–2C-alkoxy, 3–5C-cycloalkoxy, 3–5-cycloalkylmethoxy or completely or predominantly fluorine-substituted 1–2C-alkoxy, R3 is hydrogen, R31 is hydrogen, R4 is hydrogen or 1–2C-alkyl, R5 is hydrogen, R51 is hydrogen, or in which R5 and R51 together represent an additional bond, Het is an unsubstituted or R6- and/or R7-substituted radical selected from the group consisting of benzofuran-2-yl, benzofuran-3-yl, 2,3-dihydrobenzofuran2-yl, 2,3-dihydrobenzofuran-3-yl, chroman-2-yl, chroman-3-yl, chroman-4-yl, isochroman-1-yl, 1,4-benzodioxan-2-yl, 1,3-benzodioxol-2-yl, quinolin-2-yl, quinolin-4-yl, quinolin-3-yl, isoquinolin-3-yl, isoquinolin-1-yl, isoquinolin-4-yl, 1,2,3,4-tetrahydroacridin-9-yl, acridin-9-yl, indolizin-2-yl, indolizin-3-yl, indolizin-5-yl, indolizin-6-yl, indolizin-7-yl, indolizin-8-yl, phenanthridin-6-yl, cinnolin-3-yl, cinnolin-4-yl, quinazolin-4-yl, quinoxalin-2-yl, phthalazin-1-yl, 1,7-naphthyridin-3-yl, 1,6-naphthyridin-3-yl, 1,6-naphthyridin-4-yl, 1,6-naphthyridin-5-yl, 1,5-naphthyridin-2-yl, 1,5-naphthyridin-3-yl, 1,5-naphthyridin-4-yl, 1,5-naphthyridin-6-yl, 1,5-naphthyridin-7-yl, 1,5-naphthyridin-8-yl, indol-3-yl, indol-2-yl, indazol-3-yl, benzimidazol-2-yl, 2,3-dihydro-1H-indol-2-yl, 2,3-dihydro-1H-indol-3-yl, 2,3-dihydro-1H-isoindol-1-yl, 2,3-dihydro-1H-isoindol-3-yl, 1,2,3,4-tetrahydroquinolin-2-yl, 1,2,3,4-tetrahydroquinolin-3-yl, 1,2,3,4-tetrahydroquinolin-4-yl, 1,2,3,4-tetrahydroisoquinolin-1-yl, 1,2,3,4-tetrahydroisoquinolin-3-yl, 1,2,3,4-tetrahydroisoquinolin-4-yl, β-carbolin-1-yl, β-carbolin-3-yl, β-carbolin-4-yl, pyrimidin-4-yl, pyrimidin-5-yl, pyrimidin-2-yl, pyridazin-4-yl, pyridazin-3-yl and pyrazin-2-yl, where R6 is hydroxyl, halogen, nitro, amino, aminocarbonyl, 1–4C-alkyl, 1–4C-alkoxy, 1–4C-alkylcarbonyloxy, 1–4C-alkoxycarbonyl or completely or predominantly fluorine-substituted 1–2C-alkoxy, and R7 is hydroxyl, halogen, 1–4C-alkyl or 1–4C-alkoxy, or a hydrate, solvate, salt, hydrate of a salt, or solvate of a salt of that compound, or an N-oxide of that compound, or a hydrate, solvate, salt, hydrate of a salt or solvate of a salt thereof.

7. A compound of the formula I as claimed in claim 1, which has the same absolute configuration in positions 4a and 10*b* as the compound (−)-cis-1,2-dimethoxy-4-(2-aminocyclohexyl)benzene having the optical rotation $$[\alpha]_D^{20} = -58.5° \ (c = 1, \text{ethanol}),$$

which on its part is employed as a starting material.

8. A method of treating a disease or disorder treatable by the administration of PDE4 inhibitor in a patient comprising administering to said patient in need thereof a therapeutically effective amount of a PDE4 inhibiting compound of the formula I as claimed in claim 1 or a pharmaceutically acceptable hydrate, solvate, salt, hydrate of a salt, or solvate of a salt of that compound, or a pharmaceutically acceptable N-oxide of that compound, or a pharmaceutically acceptable hydrate, solvate, salt, hydrate of a salt, or solvate of a salt thereof, wherein the disease or disorder is selected from the group consisting of airway disorders, dermatoses, disorders of the arthritis type and generalized inflammations in the gastrointestinal area.

9. A pharmaceutical composition comprising at least one compound of the formula I as claimed in claim 1 or a pharmaceutically acceptable hydrate, solvate, salt, hydrate of a salt, or solvate of a salt of that compound, or a pharmaceutically acceptable N-oxide of that compound or a pharmaceutically acceptable hydrate, solvate, salt, hydrate of a salt, or solvate of a salt thereof, together with pharmaceutical excipients and/or vehicles.

10. A method of treating an airway disorder in a patient comprising administering to said patient in need thereof a therapeutically effective amount of a compound of the formula I as claimed in claim 1 or a pharmaceutically acceptable hydrate, solvate, salt, hydrate of a salt, or solvate of a salt of that compound, or a pharmaceutically acceptable N-oxide of that compound, or a pharmaceutically acceptable hydrate, solvate, salt, hydrate of a salt or solvate of a salt thereof.

11. The method according to claim 10, wherein the airway disorder is selected from the group consisting of bronchitis, allergic bronchitis, bronchial asthma, emphysema, COPD and allergic rhinitis.

* * * * *

UNITED STATES PATENT AND TRADEMARK OFFICE
CERTIFICATE OF CORRECTION

PATENT NO. : 6,884,802 B2
DATED : April 26, 2005
INVENTOR(S) : Schmidt

It is certified that error appears in the above-identified patent and that said Letters Patent is hereby corrected as shown below:

Column 20,
Line 43, please delete "thiazolyl-3-yl" and replace with -- thiazol-3-yl --.

Column 22,
Line 32, please delete "hydroXyl" and replace with -- hydroxyl --.
Line 48, please delete "R7-substitUted" and replace with -- R7-substituted --.
Line 49, please delete "bezofuran-" and replace with -- benzofuran- --.
Line 56, please delete "tetrahdroacridinyl-9-yl" and replace with
-- tetrahydroacridin-9-yl --.
Line 60, please delete "1,7-naphthyridine-3-yl" and replace with
-- 1,7-naphthyridin-3-yl --.

Column 23,
Line 13, please delete "or di-l-4C-alkylaminocarbonyl 1-4C-alkyl" and replace with
-- or di-1-4C-alkylaminocarbonyl, 1-4C-alkyl --.
Lines 30-31, please delete "3-5-cycloalkylmethoxy" and replace with
-- 3-5C-cycloalkylmethoxy --.
Line 46, please delete "dihydrobenzofuran2-yl" and replace with
-- dihydrobenzofuran-2-yl --.

Signed and Sealed this

Sixteenth Day of August, 2005

JON W. DUDAS
*Director of the United States Patent and Trademark Office*